(12) United States Patent
Linol et al.

(10) Patent No.: US 8,835,652 B2
(45) Date of Patent: Sep. 16, 2014

(54) DELTA CRYSTALLINE FORM OF THE ARGININE SALT OF PERINDOPRIL, A PROCESS FOR ITS PREPARATION, AND PHARMACEUTICAL COMPOSITIONS CONTAINING IT

(71) Applicant: Les Laboratoires Servier, Suresnes Cedex (FR)

(72) Inventors: Julie Linol, Malaunay (FR); Stephane Laurent, Valliquerville (FR); Arnaud Grenier, Breaute (FR); Sebastien Mathieu, Montivillers (FR)

(73) Assignee: Les Laboratoires Servier, rue de Verdun, Suresnes Cedex (FR)

( * ) Notice: Subject to any disclaimer, the term of this patent is extended or adjusted under 35 U.S.C. 154(b) by 0 days.

(21) Appl. No.: 13/733,339

(22) Filed: Jan. 3, 2013

(65) Prior Publication Data
US 2013/0178464 A1 Jul. 11, 2013

(30) Foreign Application Priority Data

Jan. 5, 2012 (FR) ...................... 12 00033

(51) Int. Cl.
| | |
|---|---|
| *C07D 209/42* | (2006.01) |
| *A61K 31/40* | (2006.01) |
| *A61K 45/06* | (2006.01) |
| *C07C 279/14* | (2006.01) |
| *A61K 31/4045* | (2006.01) |
| *A61K 31/4422* | (2006.01) |
| *A61K 31/198* | (2006.01) |
| *A61K 31/55* | (2006.01) |
| *A61K 31/404* | (2006.01) |
| *C07C 277/08* | (2006.01) |

(52) U.S. Cl.
CPC ............ *A61K 31/4045* (2013.01); *A61K 45/06* (2013.01); *C07C 279/14* (2013.01); *A61K 31/4422* (2013.01); *A61K 31/198* (2013.01); *A61K 31/55* (2013.01); *C07D 209/42* (2013.01); *A61K 31/404* (2013.01); *C07C 277/08* (2013.01)
USPC .......................................... 548/452; 514/412

(58) Field of Classification Search
None
See application file for complete search history.

(56) References Cited

U.S. PATENT DOCUMENTS

| | | | | |
|---|---|---|---|---|
| 4,935,525 | A * | 6/1990 | Vincent et al. ................ | 548/452 |
| 7,846,961 | B2 * | 12/2010 | Coquerel et al. ............. | 514/412 |
| 7,923,569 | B2 * | 4/2011 | Coquerel et al. ............. | 548/452 |
| 8,101,646 | B2 * | 1/2012 | Weeratunga et al. ......... | 514/412 |
| 2009/0099370 | A1 * | 4/2009 | Griesser et al. ............... | 548/452 |
| 2009/0203758 | A1 * | 8/2009 | Coquerel et al. ............. | 514/412 |
| 2011/0301357 | A1 * | 12/2011 | Jetti et al. ...................... | 548/452 |

FOREIGN PATENT DOCUMENTS

| | | |
|---|---|---|
| EP | 1354873 | 10/2003 |
| SI | 23 001 | 9/2010 |
| WO | WO 2007/099216 | 9/2007 |
| WO | WO 2007/099217 | 9/2007 |
| WO | WO 2009/157018 | 12/2009 |

OTHER PUBLICATIONS

French Preliminary Search Report for FR/1200033, of Jun. 11, 2012.
Telejko, Elwira, Current Medical Research and Opinion, vol. 23, No1 5, p. 953-960, 2007.

* cited by examiner

*Primary Examiner* — Nyeemah A Grazier
(74) *Attorney, Agent, or Firm* — Hueschen and Sage

(57) ABSTRACT

Delta crystalline form of the compound of formula (I):

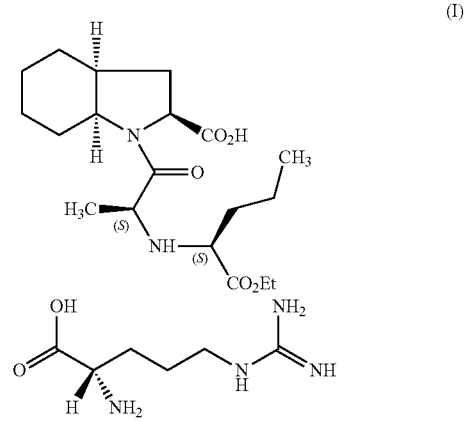

(I)

characterised by its X-ray powder diffraction diagram. Medicinal products containing the same which are useful in the treatment of cardiovascular diseases.

14 Claims, 3 Drawing Sheets

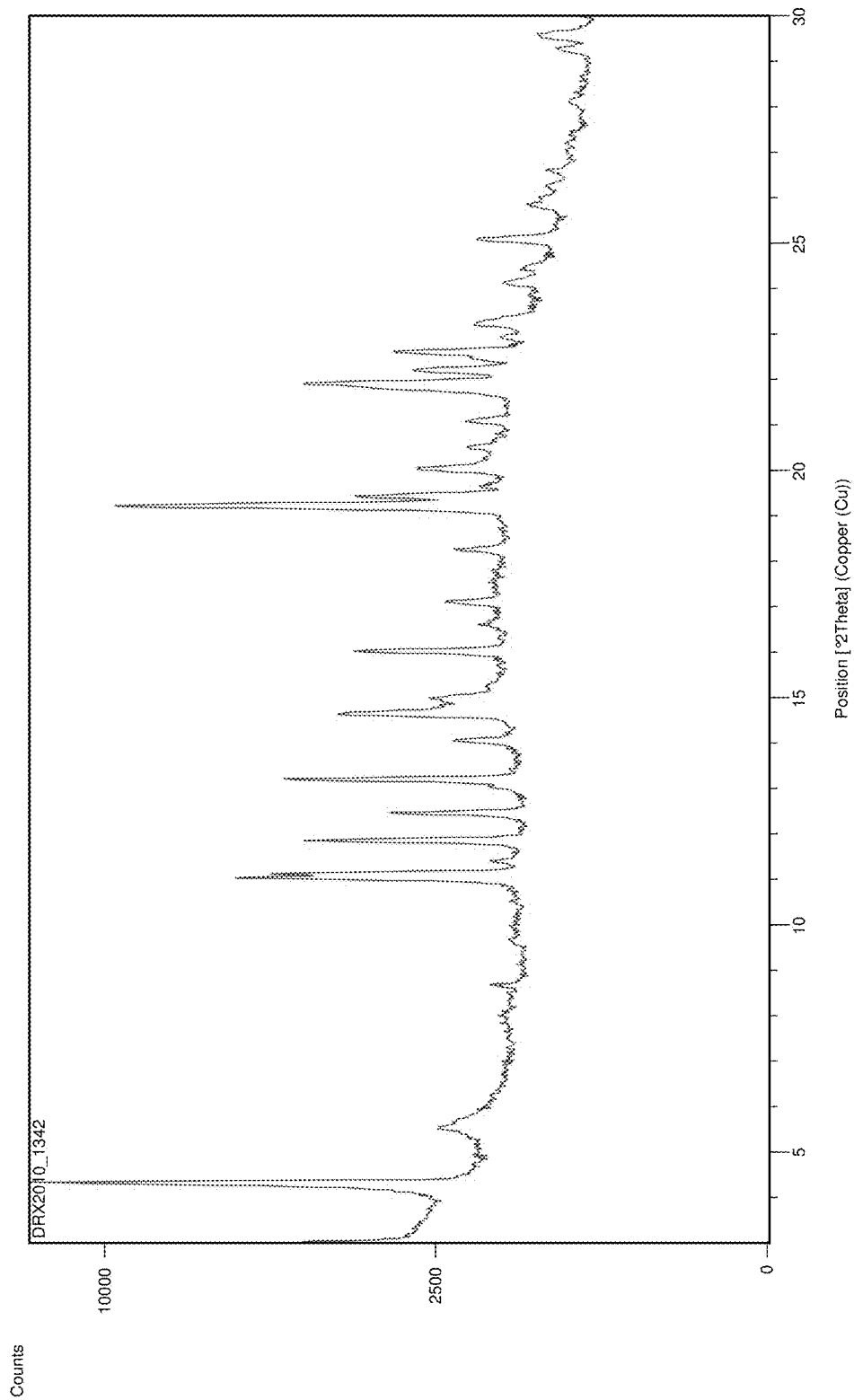
Figure 1: X-ray diffractogram of the delta form of perindopril arginine

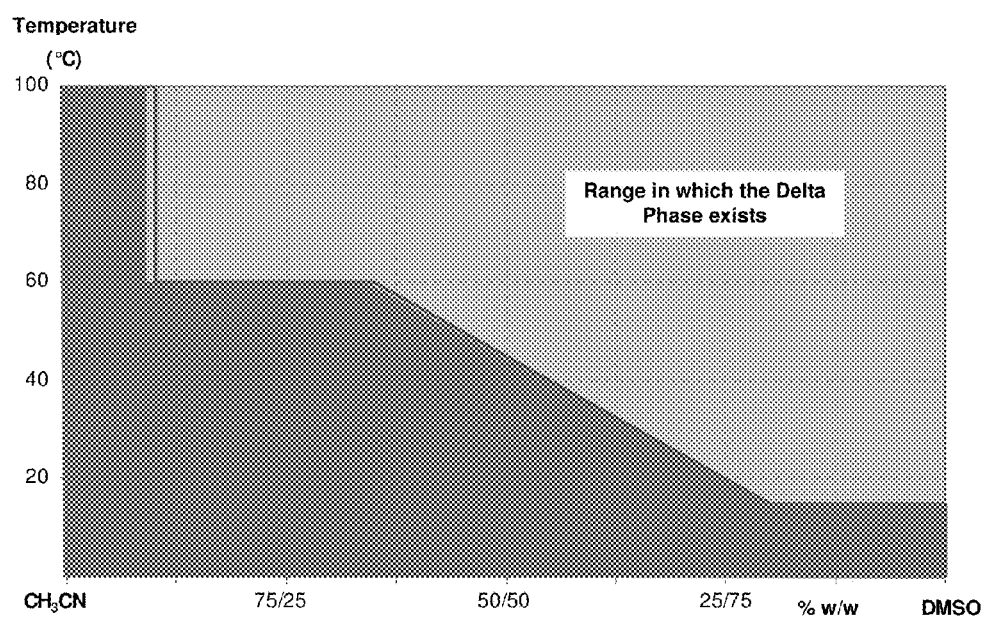
Figure 2: Simplified phase diagram of the delta form of perindopril arginine in a binary mixture of acetonitrile/dimethyl sulphoxide.

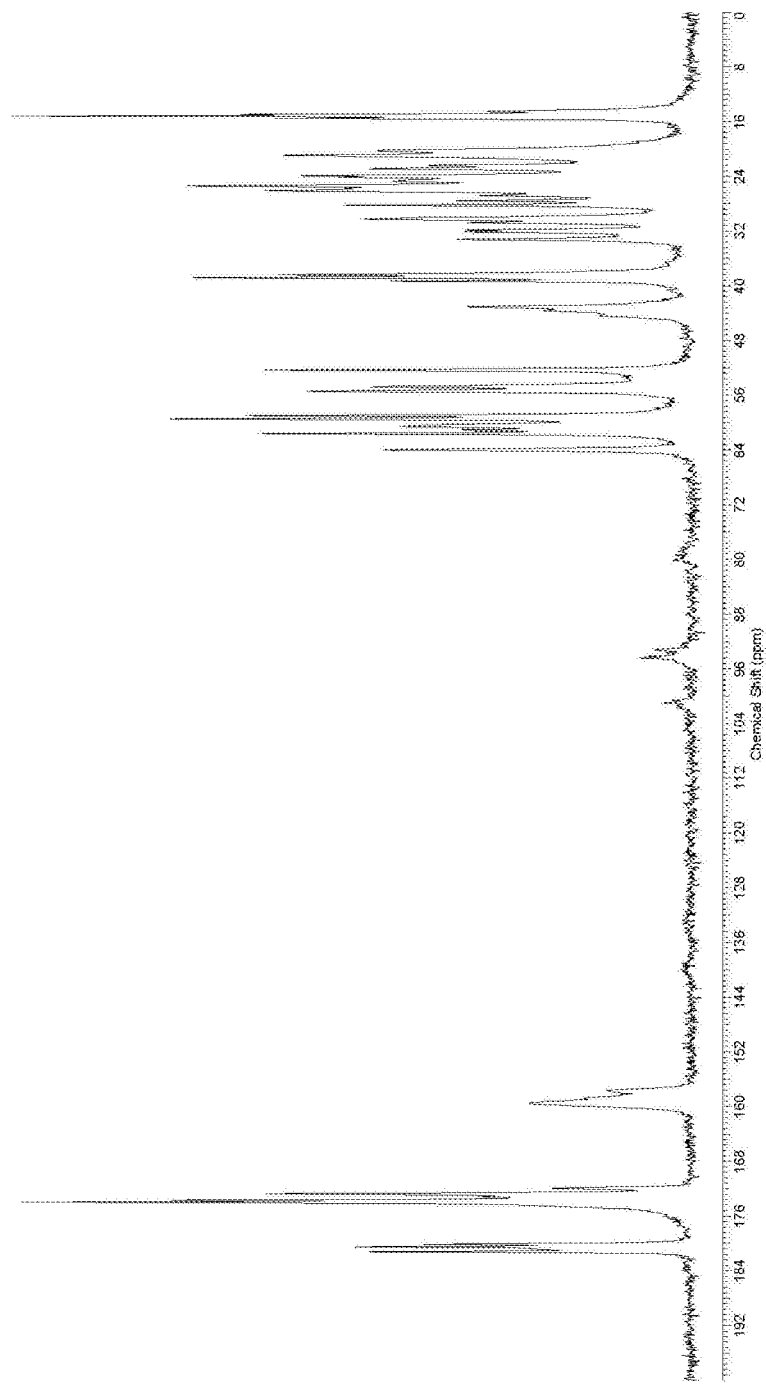
Figure 3: $^{13}$C CPMAS spectrum at 10 kHz of the delta form of perindopril arginine

DELTA CRYSTALLINE FORM OF THE ARGININE SALT OF PERINDOPRIL, A PROCESS FOR ITS PREPARATION, AND PHARMACEUTICAL COMPOSITIONS CONTAINING IT

The present invention relates to the delta crystalline form of perindopril L-arginine salt of formula (I):

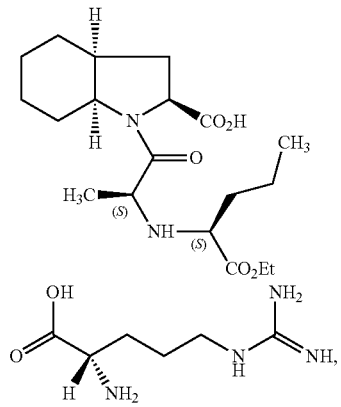

(I)

to a process for its preparation and to pharmaceutical compositions containing it.

Perindopril and its pharmaceutically acceptable salts, and more especially its arginine salt, have valuable pharmacological properties.

Their principal property is that of inhibiting angiotensin I converting enzyme (or kininase II), which makes it possible to prevent, on the one hand, conversion of the decapeptide angiotensin I to the octapeptide angiotensin II (a vasoconstrictor) and, on the other hand, degradation of bradykinin (a vasodilator) to an inactive peptide.

Those two actions contribute to the beneficial effects of perindopril in cardiovascular diseases, more especially in arterial hypertension, heart failure and stable coronary disease.

Perindopril, its preparation and its use in therapeutics have been described in European Patent specification EP 0 049 658.

The arginine salt of perindopril was first described in European Patent specification EP 1 354 873.

The alpha and beta crystalline forms of the arginine salt of perindopril have been described in European Patent specifications EP 1 989 182 and EP 2 016 051.

The gamma crystalline form of the arginine salt of perindopril has been described in Patent Application WO 2009/157018.

A process for obtaining perindopril arginine has been described in the patent specification SI 23001.

In view of the pharmaceutical value of perindopril arginine, it was of great importance to obtain it with excellent stability.

More specifically, the present invention relates to the delta crystalline form of the compound of formula (I).

The delta crystalline form of perindopril arginine according to the invention can be characterised by its X-ray diffractogram according to FIG. 1 and/or by its NMR spectrum of the solid according to FIG. 3.

In the absence of excipients and impurities, the delta crystalline form of perindopril arginine according to the invention can be characterised by the following X-ray powder diffraction diagram, measured using a diffractometer with a copper anticathode and expressed in terms of interplanar spacing d, Bragg's angle 2 theta, and relative intensity (expressed as a percentage in relation to the most intense line):

| Angle 2 theta (°) | Interplanar distance d [Å] | Relative intensity [%] |
|---|---|---|
| 4.34 | 20.37 | 66.2 |
| 5.57 | 15.86 | 5.2 |
| 11.04 | 8.02 | 57.5 |
| 11.15 | 7.94 | 47.5 |
| 11.87 | 7.454 | 35.0 |
| 12.47 | 7.09 | 17.9 |
| 13.21 | 6.70 | 33.6 |
| 14.06 | 6.30 | 6.6 |
| 14.64 | 6.05 | 31.8 |
| 16.03 | 5.53 | 17.5 |
| 17.11 | 5.18 | 5.6 |
| 18.27 | 4.85 | 4.1 |
| 19.23 | 4.61 | 100 |
| 19.44 | 4.57 | 17.8 |
| 20.04 | 4.43 | 13.6 |
| 21.11 | 4.21 | 3.7 |
| 21.93 | 4.05 | 23.0 |
| 22.20 | 4.00 | 16.9 |
| 22.61 | 3.93 | 21.2 |
| 23.21 | 3.83 | 4.5 |
| 24.30 | 3.66 | 2.3 |
| 25.09 | 3.55 | 9.4 |
| 25.95 | 3.43 | 1.7 |
| 29.54 | 3.02 | 4.2 |

Each line is considered to have an accuracy of ±0.2° in 2-theta.
The relative intensities are given for information purposes.

The X-ray powder diffraction spectrum was measured under the following test conditions:
Panalytical X'Pert Pro diffractometer
X'Celerator detector
Copper anticathode, voltage 40 kV, current 30 mA;
Transmission mounting; fixed sample;
Temperature: ambient;
Measurement range: 3° to 40°;
Increments between each measurement: 0.017°;
Measurement time per step: 49 s;
No internal standard;
Test data processed with the X'Pert Highscore software (Version 2.2a)

In the presence of impurities or excipients, especially in the presence of lactose, certain X-ray diffraction peaks of the delta form of perindopril arginine according to the invention may be masked.

Depending on the nature of excipients or impurities, the delta crystalline form of perindopril arginine according to the invention can then be characterised by the following X-ray powder diffraction peaks measured using a diffractometer with a copper anticathode and expressed in terms of angle 2-theta (°): 4.3, 11.0, 11.1, 13.2, 14.6, 16.0 and 21.9; or 4.3, 11.0, 11.1, 11.9, 13.2, 14.6, 19.2, 21.9 and 22.6; or 4.3, 11.0, 11.1, 11.9, 12.5, 13.2, 14.6, 16.0, 19.2, 19.4, 21.9, 22.2 and 22.6.

The delta crystalline form of the arginine salt of perindopril has also been characterised by solid-state NMR spectroscopy.

The solid-state $^{13}C$ NMR spectrum was recorded at ambient temperature using a Bruker SB Avance spectrometer with a 4 mm CP/MAS SB VTN type probe under the following conditions:

Frequency: 125.76 MHz,
Spectral width: 40 kHz,
Magic Angle Spinning Rate of sample: 10 kHz,
CP (Cross Polarization) pulse sequence with SPINAL64 decoupling (decoupling power of 80 kHz),
Repetition delay: 10 s,
Acquisition time: 47 ms,
Contact time: 4 ms
Number of scans: 4096.

5 Hz line-broadening was applied prior to Fourier Transformation.

The spectrum thereby obtained was referenced relative to a sample of adamantane (the high frequency peak of adamantane is set to 38.48 ppm).

The peaks observed have been collated in the following Table (expressed in terms of ppm±0.2 ppm):

| Peak no | Chemical shift (ppm) |
|---------|----------------------|
| 1       | 181.2                |
| 2       | 180.5                |
| 3       | 180.1                |
| 4       | 174.0                |
| 5       | 173.7                |
| 6       | 172.7                |
| 7       | 172.0                |
| 8       | 39.3                 |
| 9       | 38.8                 |
| 10      | 38.4                 |
| 11      | 15.6                 |
| 12      | 15.2                 |
| 13      | 15.0                 |
| 14      | 14.5                 |

The invention relates also to a process for the preparation of the delta crystalline form of the arginine salt of perindopril by crystallisation or recrystallisation of perindopril arginine salt from a binary mixture of acetonitrile, ethyl acetate or methyl tert-butyl ether and dimethyl sulphoxide or a ternary mixture of acetonitrile, dimethyl sulphoxide and toluene, at a temperature higher than 20° C.

In the case of a process by crystallisation, the arginine salt of perindopril may be obtained starting from another perindopril salt, for example the tert-butylamine salt, which is reacted with an acid to obtain perindopril in free acid form, which is converted into a salt by arginine in a binary mixture of acetonitrile, ethyl acetate or methyl tert-butyl ether and dimethyl sulphoxide or a ternary mixture of acetonitrile, dimethyl sulphoxide and toluene.

In the case of a process by recrystallisation, the perindopril arginine salt used as starting material may be in anhydrous or hydrated form, in amorphous form or in any crystalline form.

When a binary mixture of acetonitrile, ethyl acetate or methyl tert-butyl ether and dimethyl sulphoxide is used, the ratio of acetonitrile/dimethyl sulphoxide, ethyl acetate/dimethyl sulphoxide or methyl tert-butyl ether/dimethyl sulphoxide is preferably between 90/10 w/w and 10/90 w/w, the limits being inclusive.

The temperature of the medium during crystallisation or recrystallisation is preferably between 25° C. and 80° C., inclusive, more preferably between 60 and 80° C., inclusive.

The mixture may advantageously be seeded during the cooling step ("with seeding" mode).

When the mixture is not seeded ("without seeding" mode), the time in contact with the mixture of solvents is preferably greater than 6 hours.

The invention relates also to pharmaceutical compositions comprising as active ingredient the delta crystalline form of the compound of formula (I) together with one or more appropriate, non-toxic, inert excipients. Among the pharmaceutical compositions according to the invention there may be more especially mentioned those that are suitable for oral, parenteral (intravenous or subcutaneous) or nasal administration, tablets or dragées, sublingual tablets, capsules, lozenges, suppositories, creams, ointments, dermal gels, injectable preparations and drinkable suspensions.

The pharmaceutical composition in tablet form is preferably prepared by direct compression. The useful dosage can be varied according to the nature and severity of the disorder, the administration route and also the age and weight of the patient. The useful dosage varies from 1 mg to 20 mg per day in one or more administrations, preferably from 2.5 to 10 mg in one administration per day.

The pharmaceutical compositions according to the invention may also comprise one or more other active ingredients selected from diuretics such as indapamide, calcium antagonists such as amlodipine and If current inhibitors such as ivabradine.

When the pharmaceutical compositions according to the invention also comprise indapamide, the amount of indapamide is preferably between 0.625 and 2.5 mg, the limits being inclusive.

When the pharmaceutical compositions according to the invention also comprise amlodipine, the amount of amlodipine is preferably between 5 and 10 mg, the limits being inclusive.

When the pharmaceutical compositions according to the invention also comprise ivabradine, the amount of ivabradine is preferably between 5 and 30 mg, the limits being inclusive.

The following Examples illustrate the invention.

In Examples 1 to 4 hereinbelow, the perindopril arginine salt used as starting material had a water content of about 3 to 4%.

FIG. 1: Diffractogram of the delta form of perindopril arginine.

FIG. 2: Phase diagram of the delta form of perindopril arginine in a binary mixture of acetonitrile/dimethyl sulphoxide.

FIG. 3: NMR spectrum of the solid of the delta form of perindopril arginine

ABBREVIATIONS

CPMAS Cross Polarization Magic Angle Spinning
DMSO dimethyl sulphoxide
w/w ratio expressed in terms of weight/weight
NMR Nuclear Magnetic Resonance

EXAMPLE 1

Delta Crystalline Form of the Arginine Salt of Perindopril (Binary Mixture of Acetonitrile/Dimethyl Sulphoxide 25/75 w/w, "without Seeding" Mode)

55.32 g of perindopril arginine salt, 297.50 g of dimethyl sulphoxide and 94.49 g of acetonitrile are introduced into a reactor.

The mixture is heated, with stirring, at 70° C. for 7 hours, and then cooled to 40° C. at 1° C./min. After 30 minutes at 40° C., the mixture is filtered over a glass frit. The filter cake is washed with ethyl acetate and dried overnight at 50° C. in a fan-circulation oven to yield the delta crystalline form of perindopril arginine in a yield of 54%.

EXAMPLE 2

Delta Crystalline Form of the Arginine Salt of Perindopril (Binary Mixture of Acetonitrile/Dimethyl Sulphoxide 25/75 w/w, "with Seeding" Mode)

52.2 g of perindopril arginine salt, 216 g of dimethyl sulphoxide and 76 g of acetonitrile are introduced into the reactor.

The mixture is heated, with stirring, to 70° C. At 70° C., 0.52 g of the delta form of perindopril arginine are added in order to initiate crystallisation.

The mixture is heated at 70° C. for 5 hours (until stabilisation of the turbidity curve) and then cooled to 40° C. at 0.5° C/min. After 30 minutes at 40° C., the mixture is filtered through a filtering medium (diameter=5 cm, filtration threshold=20 microns) in a 1 L stainless-steel cell.

The filter cake is washed with ethyl acetate and dried overnight at 50° C. in a fan-circulation oven.

The delta crystalline form of perindopril arginine is obtained in a yield of 72% (seed subtracted).

EXAMPLE 3

Delta Crystalline Form of the Arginine Salt of Perindopril (Binary Mixture of Acetonitrile/Dimethyl Sulphoxide 10/90 w/w, "with Seeding" Mode)

280 g of perindopril arginine salt, 950 g of dimethyl sulphoxide and 97 g of acetonitrile are introduced into a 2 L reactor.

The suspension is heated to 80° C. and is seen to pass into solution. The mixture is maintained at 80° C. for 5 minutes and then cooled to 70° C. at a rate of 0.5° C./min. Once the temperature of the mixture is at 70° C., acetonitrile is added (197 g, pouring time=20 minutes). At the end of the addition, the mixture remains clear. The solution is seeded with 6 g of the delta form of perindopril arginine. A stage at 70° C. is applied for 45 minutes.

The suspension is cooled to 25° C. at a rate of 0.5° C./min. The contact time at 25° C. is 4 hours before filtration using a 2 L cell. The filter cake is washed with ethyl acetate and dried overnight at 50° C. in a fan-circulation oven. The delta crystalline form of perindopril arginine is obtained in a yield of 91% (seed subtracted).

EXAMPLE 4

Delta Crystalline Form of the Arginine Salt of Perindopril (Binary Mixture of Acetonitrile/Dimethyl Sulphoxide 10/90 w/w, "at 25° C." Mode)

25 g of perindopril arginine salt and 90 g of the binary mixture acetonitrile/dimethyl sulphoxide 10/90 (w/w) are introduced into a reactor with mechanical stirring. After being in contact for 72 hours at 25° C. with stirring, the transition to the delta form is complete.

The reaction mixture is then filtered to result in isolation of the delta crystalline form of perindopril arginine in a yield of 79%.

EXAMPLE 5

Delta Crystalline Form of the Arginine Salt of Perindopril Starting from Perindopril (Free Acid), in a Binary Mixture of Acetonitrile/DMSO 25/75

Perindopril (12.5 g, 1 eq.) and L-arginine (5.32 g–0.9 eq) are suspended in a mixture of acetonitrile (20 g, d=0.787) and DMSO (61 g, d=1.100). The reaction mixture is heated at 50° C. overnight. The product is then isolated by filtration over a frit. The filter cake is washed and dried.

The delta crystalline form of perindopril arginine is obtained in a yield of 79% relative to the perindopril.

EXAMPLE 6

Delta Crystalline Form of the Arginine Salt of Perindopril (Binary Mixture of Ethyl Acetate/dimethyl Sulphoxide 70/30 w/w, "with Seeding" Mode)

15 g of perindopril arginine and 43.6 g of DMSO are introduced into a 0.5L reactor. The concentration of the perindopril arginine in the mixture is 25.6% (percent by weight). The mixture is heated to about 70° C. and then 102 g of ethyl acetate are added over 20 minutes (ratio of ethyl acetate/DMSO: 70/30 w/w).

The mixture is seeded at 70° C. with 0.3 g of the delta crystalline form. After seeding, the mixture is maintained at 70° C., with stirring, for 2 hours. Cooling to 20° C. at a rate of 0.2° C/min is applied, followed by a contact time of 16 hours.

Isolation of the product is carried out over a filtration medium (porosity 0.41 µm) in a cell.

The solid is washed once with a mixture of ethyl acetate/DMSO and twice with ethyl acetate and is dried in an oven in vacuo at 50° C.

The delta crystalline form of perindopril arginine is obtained in a yield of 93% (seed subtracted).

EXAMPLE 7

Pharmaceutical Composition

Formula for the preparation of 1000 tablets each containing 5 mg of active ingredient:

| | |
|---|---|
| Delta form of perindopril arginine | 5 g |
| Hydroxypropylcellulose | 2 g |
| Wheat starch | 10 g |
| Lactose | 100 g |
| Magnesium stearate | 3 g |
| Talc | 3 g |

EXAMPLE 8

Pharmaceutical Composition

Tablet containing 10 mg of perindopril arginine, with a final weight of 100 mg:

| | |
|---|---|
| Delta form of perindopril arginine | 10 mg |
| Lactose monohydrate | 64.2 mg |
| Microcrystalline cellulose | 25 mg |
| Magnesium stearate | 0.5 mg |
| Anhydrous colloidal silica | 0.3 mg |

EXAMPLE 9

Thermal Stability

The thermal stability of the delta form at 110° C. in an open flask was compared to that of forms from the prior art.

The results are as follows:

| Crystalline form | Conditions | HPLC purity (%) |
| --- | --- | --- |
| α form according to EP 1 989 182 | t = 0 | 99.8 |
| | 76 hours at 110° C. | 98.8 |
| β form according to EP 2 016 051 | t = 0 | 99.6 |
| | 76 hours at 110° C. | 98.3 |
| γ form according to WO 2009/157018 | t = 0 | 99.7 |
| | 76 hours at 110° C. | 93.4 |
| Amorphous form | t = 0 | 99.3 |
| | 76 hours at 110° C. | 91.0 |
| Form obtained according to the process of SI 23001 | t = 0 | 99.1 |
| | 76 h at 110° C. | 86.9 |
| δ form according to the present invention | t = 0 | 99.7 |
| | 76 hours at 110° C. | 99.5 |

These results show that the delta crystalline form of perindopril arginine salt has improved thermal stability compared to the other known forms.

The invention claimed is:

1. A delta crystalline form of perindopril L-arginine salt of formula (I):

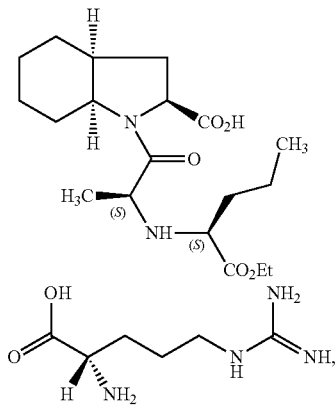

(I)

having the following X-ray powder diffraction peaks measured using a diffractometer with a copper anticathode and expressed in terms of Bragg's angle 2 theta (°): 4.3, 11.0, 11.1, 13.2, 14.6, 16.0 and 21.9.

2. The delta crystalline form according to claim 1, having the following X-ray powder diffraction peaks measured using a diffractometer with a copper anticathode and expressed in terms of Bragg's angle 2 theta: 4.3, 11.0, 11.1, 11.9, 12.5, 13.2, 14.6, 16.0, 19.2, 19.4, 20.0, 21.9, 22.2 and 22.6.

3. The delta crystalline form according to claim 1, having the following X-ray powder diffraction diagram measured using a diffractometer with a copper anticathode and expressed in terms of interplanar spacing d, Bragg's angle 2 theta, and relative intensity expressed as a percentage in relation to the most intense line:

| Angle 2 theta (°) | Interplanar distance d [Å] | Relative intensity [%] |
| --- | --- | --- |
| 4.34 | 20.37 | 66.2 |
| 5.57 | 15.86 | 5.2 |
| 11.04 | 8.02 | 57.5 |
| 11.15 | 7.94 | 47.5 |
| 11.87 | 7.454 | 35.0 |
| 12.47 | 7.09 | 17.9 |
| 13.21 | 6.70 | 33.6 |
| 14.06 | 6.30 | 6.6 |
| 14.64 | 6.05 | 31.8 |
| 16.03 | 5.53 | 17.5 |
| 17.11 | 5.18 | 5.6 |
| 18.27 | 4.85 | 4.1 |
| 19.23 | 4.61 | 100 |
| 19.44 | 4.57 | 17.8 |
| 20.04 | 4.43 | 13.6 |
| 21.11 | 4.21 | 3.7 |
| 21.93 | 4.05 | 23.0 |
| 22.20 | 4.00 | 16.9 |
| 22.61 | 3.93 | 21.2 |
| 23.21 | 3.83 | 4.5 |
| 24.30 | 3.66 | 2.3 |
| 25.09 | 3.55 | 9.4 |
| 25.95 | 3.43 | 1.7 |
| 29.54 | 3.02 | 4.2. |

4. The delta crystalline form according to claim 1, having a solid-state $^{13}$C CPMAS NMR spectrum exhibiting the following peaks, expressed in ppm:

| Peak no. | Chemical shift (ppm) |
| --- | --- |
| 1 | 181.2 |
| 2 | 180.5 |
| 3 | 180.1 |
| 4 | 174.0 |
| 5 | 173.7 |
| 6 | 172.7 |
| 7 | 172.0 |
| 8 | 39.3 |
| 9 | 38.8 |
| 10 | 38.4 |
| 11 | 15.6 |
| 12 | 15.2 |
| 13 | 15.0 |
| 14 | 14.5. |

5. A process for the preparation of the delta crystalline form according to claim 1, comprising crystallisation or recrystallisation from a binary mixture of acetonitrile, ethyl acetate or methyl tert-butyl ether and dimethyl sulphoxide or a ternary mixture of acetonitrile, dimethyl sulphoxide and toluene, at a temperature higher than 20° C.

6. The process according to claim 5, wherein the binary mixture of acetonitrile, ethyl acetate or methyl tort-butyl ether and dimethyl sulphoxide has a ratio of acetonitrile/dimethyl sulphoxide, ethyl acetate/dimethyl sulphoxide or methyl tert-butyl ether/dimethyl sulphoxide ranging from 90/10 w/w to 10/90 w/w.

7. The process according to claim 5, wherein the temperature of the medium is between 25 and 80° C., inclusive.

8. The process according to claim 7, wherein the mixture is heated to a temperature of from 60 to 80° C.

9. The process according to claim 5, wherein the mixture is seeded with the delta crystalline form.

10. A pharmaceutical composition comprising, as active ingredient. the delta crystalline form according to claim 1, in combination with one or more inert, non-toxic, pharmaceutically acceptable carriers.

11. The pharmaceutical composition according to claim 10, further comprising a diuretic, a calcium antagonist or an If current inhibitor.

12. The pharmaceutical composition according to claim 11, wherein the diuretic is indapamide.

13. The pharmaceutical composition according to claim 11, wherein the calcium antagonist is amlodipine.

14. The pharmaceutical composition according to claim 11, wherein the if current inhibitor is ivabradine.

\* \* \* \* \*

UNITED STATES PATENT AND TRADEMARK OFFICE
CERTIFICATE OF CORRECTION

| | | |
|---|---|---|
| PATENT NO. | : 8,835,652 B2 | Page 1 of 1 |
| APPLICATION NO. | : 13/733339 | |
| DATED | : September 16, 2014 | |
| INVENTOR(S) | : Julie Linol et al. | |

It is certified that error appears in the above-identified patent and that said Letters Patent is hereby corrected as shown below:

In the Claims

Column 9, Line 9: "if" should be --If--.

Signed and Sealed this
Twenty-third Day of December, 2014

Michelle K. Lee
*Deputy Director of the United States Patent and Trademark Office*